US006659982B2

(12) United States Patent
Douglas et al.

(10) Patent No.: US 6,659,982 B2
(45) Date of Patent: *Dec. 9, 2003

(54) MICRO INFUSION DRUG DELIVERY DEVICE (75) Inventors: Joel Douglas, Los Altos Hills, CA (US); Robert Hugo, Jr., Gilroy, CA (US)

(73) Assignee: Sterling Medivations, Inc., Norcross, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/845,256

(22) Filed: May 1, 2001

(65) Prior Publication Data

US 2001/0053887 A1 Dec. 20, 2001

Related U.S. Application Data (63) Continuation-in-part of application No. 09/672,103, filed on Sep. 29, 2000, now Pat. No. 6,482,186, and a continuation-in-part of application No. 09/672,456, filed on Sep. 29, 2000.
(60) Provisional application No. 60/202,818, filed on May 8, 2000, and provisional application No. 60/223,630, filed on Aug. 8, 2000.

(51) Int. Cl.[7] .......................... A61M 5/00; A61M 1/00; A61M 5/32
(52) U.S. Cl. ................. 604/173; 604/117; 604/152; 604/187; 604/272
(58) Field of Search ............... 604/93.01, 117, 604/174, 180, 187, 264, 272, 533–535, 890.1, 891.1, 151, 154, 152, 164.09, 258, 173

(56) References Cited

U.S. PATENT DOCUMENTS 3,595,231 A    7/1971   Pistor
3,814,097 A    6/1974   Ganderton et al.
3,963,380 A    6/1976   Thomas, Jr. et al.
3,964,482 A    6/1976   Gerstel et al.
3,964,484 A    6/1976   Reynolds et al.
4,235,234 A   11/1980   Whitney
4,276,878 A    7/1981   Storz (List continued on next page.)

FOREIGN PATENT DOCUMENTS

EP   0 295 075   12/1988
EP   0 323 321    7/1989
EP   0 916 353    5/1999

(List continued on next page.)

OTHER PUBLICATIONS

Co–pending application # 09/672,456.*
Albisser, A.M., et al., "A Portable Precision Pumping System for Chronic, Programmed Insulin Infusion", Medical Progress Through Technology, 1978, vol. 5, pp. 187–193.

(List continued on next page.)

Primary Examiner—Brian L. Casler
Assistant Examiner—Catherine Serke
(74) Attorney, Agent, or Firm—Burns, Doane, Swecker & Mathis, L.L.P.

(57) ABSTRACT

An infusion pump includes a plurality of projections configured so that they enter the subcutaneous region of the patients skin and provides a painless means of creating a breach in the stratum corneum which is sealed against leakage by the skin surrounding each projection and provides a flow path for either a basal and bolus injection of medication. The pump includes a drug reservoir containing a drug. The pump includes a microactuator and includes a housing having a foundation or lid which opens and closes so that the medication container can be inserted and supported in a delivery mode position. A micro actuator is used to advance either a roller or a piston in communication with the medication container. Attached to the micro-actuator is a device that is mounted for movement along the access of the medication container. The device indexes along the medication container that is used to dispense the medication.

5 Claims, 10 Drawing Sheets

U.S. PATENT DOCUMENTS

| | | | |
|---|---|---|---|
| 4,313,439 A | | 2/1982 | Babb et al. |
| 4,493,704 A | | 1/1985 | Beard et al. |
| 4,645,495 A | * | 2/1987 | Vaillancourt ................. 604/180 |
| 4,741,736 A | | 5/1988 | Brown |
| 4,813,939 A | * | 3/1989 | Marcus ....................... 604/177 |
| 4,856,340 A | | 8/1989 | Garrison |
| 4,865,591 A | | 9/1989 | Sams |
| 4,883,472 A | | 11/1989 | Michel |
| 4,969,871 A | | 11/1990 | Theeuwes et al. |
| 4,973,318 A | | 11/1990 | Holm et al. |
| 5,017,190 A | | 5/1991 | Simon et al. |
| 5,026,357 A | | 6/1991 | Przuntek et al. |
| 5,261,882 A | | 11/1993 | Sealfon |
| 5,279,586 A | | 1/1994 | Balkwill |
| 5,327,033 A | | 7/1994 | Guckel et al. |
| 5,330,431 A | | 7/1994 | Herskowitz |
| 5,354,279 A | * | 10/1994 | Hofling ................. 604/164.12 |
| 5,391,250 A | | 2/1995 | Cheney, II et al. |
| 5,419,777 A | * | 5/1995 | Hofling ....................... 604/264 |
| 5,437,999 A | | 8/1995 | Diebold et al. |
| 5,464,395 A | * | 11/1995 | Faxon et al. ........... 604/103.02 |
| 5,587,326 A | | 12/1996 | Takemura |
| 5,637,095 A | | 6/1997 | Nason et al. |
| 5,640,995 A | | 6/1997 | Packard et al. |
| 5,644,177 A | | 7/1997 | Guckel et al. |
| 5,697,901 A | | 12/1997 | Eriksson |
| 5,716,343 A | * | 2/1998 | Kriesel et al. .............. 604/132 |
| 5,914,507 A | | 6/1999 | Polla et al. |
| 5,957,889 A | | 9/1999 | Poulsen et al. |
| 5,964,729 A | | 10/1999 | Choi et al. |
| 5,997,501 A | | 12/1999 | Gross et al. |
| 6,016,693 A | | 1/2000 | Viani et al. |
| 6,022,316 A | | 2/2000 | Eppstein et al. |
| 6,050,988 A | * | 4/2000 | Zuck ....................... 604/890.1 |
| 6,083,196 A | | 7/2000 | Trautman et al. |
| 6,132,755 A | | 10/2000 | Eicher et al. |
| 6,256,533 B1 | | 7/2001 | Yuzhakov et al. |
| 6,302,870 B1 | * | 10/2001 | Jacobsen et al. ............ 604/272 |

FOREIGN PATENT DOCUMENTS

| | | |
|---|---|---|
| EP | 0 937 475 | 8/1999 |
| FR | 2 628 636 | 9/1989 |
| WO | WO 93/17754 | 9/1993 |
| WO | WO 95/09021 | 4/1995 |
| WO | 96/38190 | 12/1996 |
| WO | WO 97/36623 | 10/1997 |
| WO | 98/57688 | 12/1998 |
| WO | 99/47341 | 9/1999 |
| WO | 99/64580 | 12/1999 |
| WO | 00/16833 | 3/2000 |
| WO | 00/35530 | 6/2000 |

OTHER PUBLICATIONS

Tamborlane, W., et al., "Reduction to Normal of Plasma Glucose in Juvenile Diabetes by Subcutaneous Administration of Insulin with a Portable Infusion Pump", The New England Journal of Medicine, 1979, vol. 300, pp. 573–578.

Co–pending patent application Ser. No. 60/202,818, filed May 8, 2000, inventor: Joel Douglas.

Co–pending patent application Ser. No. 60/223,630, filed Aug. 8, 2000, inventor: Joel Douglas.

Co–pending patent application Ser. No. 09/672,103, filed Sep. 29, 2000, inventor: Joel Douglas et al.

Co–pending patent application Ser. No. 09/672,456, filed Sep. 29, 2000, inventor: Joel Douglas.

* cited by examiner

MICRO INFUSION DRUG DELIVERY DEVICE

This application is related and claim priority to: U.S. application Ser. No. 60/202,818, filed May 8, 2000, U.S. application Ser. No. 60/223,630, filed Aug. 8, 2000, a continuation-in-part of U.S. application Ser. No. 09/672,103, filed Sep. 29, 2000 now U.S. Pat. No. 6,482,186, and a continuation-in-part of U.S. application Ser. No. 09/672,456, filed Sep. 29, 2000, the entire contents of each of which is incorporated by reference herein.

BACKGROUND OF THE INVENTION

1. Field of the Invention

This invention relates in general to methods and apparatus for infusing medications into a patient subcutaneously. In particular, the invention relates to an infusion pump that is adapted for use with prepackaged containers for delivering medications to patients from the container to the subcutaneous region of the patient via a catheter or needle, and to infusion needle array devices.

2. Brief Description of the Related Art

Infusion sets and pumps are used to deliver various types of solutions subcutaneously to patients. There are many medical conditions that require the administration of liquid medicaments transcutaneously (through the skin) and subcutaneously for prolonged periods. Diabetes, for example, may be controlled by daily, or more frequent, injections of insulin. The ability to administer numerous small dosages of insulin has been proven to be the best way to insure tight glucose control for a patient. The National Institute of Health (NIH) conducted a long-term study of people with diabetes known as the Diabetes Complications and Control Trial (DCCT) were it was determined that the proper management of diabetes requires 4 or more injections of insulin per day. However, current devices either are not convenient, painless enough, or easy to use by patients. Syringes and insulin pens all require the patients to inject themselves and do not provide a convenient or discreet mechanism to accomplish medication delivery.

Since transcutaneous injections are painful and troublesome, and since each injection represents a possibility for infection, injections are spaced at intervals as far apart as possible, resulting in peak and valley concentrations of the medicament in the bloodstream or at the site in the body requiring the medicament, the peak concentrations occurring shortly after the administration of the medicament and the low, or valley, concentrations occurring shortly before the administration of the next injection. This method of administration exposes the patient to the possibility of overdose at peak levels and underdose at valley levels, but was nevertheless the standard method for many years in the absence of a better alternative.

Recently, systems have been developed in which a catheter is semi-permanently implanted in a patient to provide access to a transcutaneous site in a patient's body, and a liquid medicament is supplied to the catheter from a reservoir. However, many patients find that the infusion site forms small red marks that are the result of irritation from the infusion at a single point. Infusing the medication either by bolus injection or reducing the amount of medication infused at any one specific site relieves this irritation.

Insigler and Kirtz (Diabetics, 28: 196–203, 1979) describe a portable insulin dosage regulating apparatus which uses an electrically driven mini-pump with an insulin reservoir to periodically dispense a predetermined number of insulin units (U). A small electronic control box is used to set the basal rate of 0.4 U/hr in stages of 0.2 U each. A switch is used to trigger a program that infuses a higher dose for a period of one hour, after which the system automatically goes back to the basal rate.

Thomas et al. U.S. Pat. No. 3,963,380, issued Jun. 15, 1976, describes a micropump driven by piezoelectric disk benders. Although the pump draws only a small current, it requires a voltage of about 100 volts to drive the pump.

Tamborlane et al. (*The New England Journal of Medicine*, 300: 573–578, No. 11, Mar. 15, 1979) describe a portable subcutaneous insulin delivery system which uses a battery driven syringe pump. The apparatus is bulky and heavy.

A peristaltic motor driven pump has been described by Albisser et al. (Med. Progr. Technol. 5: 187–193 [1978]). The pump weighs 525 g. and consumes 60 milliwatts at maximum pumping rates. This system has a continuous duty cycle. It is bulky and heavy and consumes a relatively large amount of power.

Additionally, a number of devices have been developed for administering insulin, drugs, or other substances to persons and animals. As self-administration of certain substances, such as insulin, is common, it is important that devices designed for self-administration be simple to operate, reliable, and accurate. The current devices available for the patient include syringes, pumps, or injection pens. Each of these devices do not provide for both a convenient, easy to use, and discreet means of injecting medication. The patients must inject themselves either in public, or use expensive bulky devices.

The different types of infusion pumps in the prior art include elastomeric pumps which squeeze the solution from flexible containers, such as balloons, into tubing for delivery to the patient. Spring loaded pumps have also been provided to pressurize the solution containers or reservoirs. Infusion pumps have also been provided with cartridges containing flexible compartments that are squeezed by pressure rollers for discharging the solutions, such as the pump shown in U.S. Pat. No. 4,741,736. These types of infusion pumps, however, require special containers and are not adaptable for using standard pre-filled single dose containers for solutions.

Where infusion pumps cannot use the standard pre-filled single dose containers, it is necessary to separately fill the containers with the medication from larger vials. The transfer of medication to the cartridges, balloons, reservoirs and other specialized containers is a difficult and problematic process for people with chronic illnesses such as diabetes who must take insulin to adequately process their glucose. The need has therefore been recognized for an infusion pump system which obviates the limitations and disadvantages of existing pumps of this type, and which is adapted for use with standard pre-filled single dose containers Additionally, the currently available devices for infusing medication subcutaneously require the patient to insert a needle or flexible catheter through the skin into the subcutaneous region. Patients find this either painful, inconvenient, or very invasive. The result is that the majority of patients do not utilize pumps and infusion sets which have a major advantage over traditional injection therapy consisting of periodic injections with syringes.

Morphologically, the composite epithelial layer of the skin, also called the epidermis, is the part of the skin endowed with the barrier against penetration, and it consists of four layers. These layers are an outermost layer called the stratum corneum and three underlying layers, called the stratum granulosum, the stratum malpighii, and the stratum germinativum. The stratum corneum is a heterogenous layer of flattened, relatively dry, keratinised cells with a dense underlying layer commonly called the horny layer. In the past, it was generally held that this horny layer acted as the barrier to the penetration of external substances into the body. See J. Invest. Dermat., Vol 50, pages 19 to 26, 1968. Now, it is generally held that the whole stratum corneum and not a discrete cellular layer functions as a barrier to the penetration of substances into the body. The whole stratum corneum is considered to be a barrier because of a chemical keratin-phospholipid complex that exists in the stratum corneum and acts along with the horny layer as a barrier to the penetration of substances into the body. For the purposes of the present invention, the whole stratum corneum is considered as the natural barrier to penetration. J. Invest. Dermat., Vol 50, pages 371 to 379, 1968; and, ibid, Vol 56, pages 72 to 78, 1971.

The stratum corneum, which is about 15 microns thick when dry and about 48 microns thick when filly hydrated, acts as a barrier for an extremely large variety of compounds. The barrier is maintained for compounds with large molecular volumes, for compounds substituted with functional groups, for small soluble molecules, for non-electrolytes, and the like. See J. Invest. Dermat., Vol 52, pages 63 to 70, 1969. Once a compound is made to pass through the stratum corneum, for example, by surgically stripping the stratum corneum, there is no major hindrance to penetration of the remaining epidermal layers or the dermis. After this, the compound enters into the circulation via the capillaries. See *Progress in the Biological Sciences in Relation to Dermatology*, 2nd Ed., pages 245, 1964, Univ. Press, Cambridge; and, J. of Drug and Cosmetic Ind., Vol 108, No. 2, pages 36 to 39 and 152 to 154, 1971.

In view of the above presentation, once a drug has penetrated through the stratum corneum, for example with the aid of the drug delivery device of the present invention, penetration through the remaining layers of the skin proceeds readily. However, drugs such as insulin must be delivered into the dermal area, that is, between the superficial vascular plexus and the deep vascular plexus, to insure uniform and consistent absorption by the body. Absorption of a drug into the stratum corneum with no further penetration is considered retention and not percutaneous penetration.

Other prior devices and methods include U.S. Pat. No. 3,964,484, U.S. Pat. No. 4,235,234, U.S. Pat. No. 4,969,871, U.S. Pat. No. 6,083,196, U.S. Pat. No. 6,050,988, U.S. Pat. No. 5,587,326, U.S. Pat. No. 6,022,316, U.S. Pat. No. 4,883,472, U.S. Pat. No. 4,865,591, U.S. Pat. No. 4,973,318, U.S. Pat. No. 5,017,190, U.S. Pat. No. 5,279,586, U.S. Pat. No. 4,856,340, U.S. Pat. No. 4,313,439, U.S. Pat. No. 5,640,995, and U.S. Pat. No. 5,327,033, the contents of each of the which is incorporated herein by reference in their entirety.

Various micro actuators have been developed to drive a variety of mechanisms including pumps and linear motion devices. The development of these devices does not provide a small enough or low cost discrete solution to medication delivery. From a review of the current art for expelling medication from a prefilled cartridge it is clear that the devices are of substantial size and bulky.

U.S. Pat. No. 5,644,177 discloses micromechanical structures capable of actuation for purposes such as fluid flow control which are formed on substrates in sizes in the range of one or two millimeters or less using micromechanical processing techniques. A magnetic core having a gap therein is fixed on the substrate, and a plunger is mounted by a spring for movement parallel to the substrate in response to the flux provided to the gap of the fixed core. An electrical coil wound around a mandrel is engaged to the fixed magnetic core such that flux is induced in the core when current is supplied to the coil, driving the plunger against the force of the spring. A micromechanical fluid control unit includes a metal frame structure formed by electrodeposition on a substrate with the inner wall of the frame having slots formed therein to admit a separator wall which divides the interior of the frame into separate chambers, with a cover secured over the top of the frame and the separator wall to seal the chambers. A plunger actuator can be mounted within the frame with fixed core sections extending through the walls of the frame, and with the mandrel and coil engaged to the fixed core sections outside of the frame to provide magnetic flux to a gap to actuate the plunger within the sealed enclosure.

U.S. Pat. No 5,914,507 discloses a micromechanical device or microactuator based upon the piezoelectric, pyroelectric, and electrostrictive properties of ferroelectric thin film ceramic materials such as PZT. The microdevice has a device substrate and a deflectable component. The deflectable component is mounted for deflection on the device substrate and has a sensor/actuator. The sensor/actuator has first and second electrodes and a piezoelectric thin film disposed between the first and second electrodes. The thin film is preferably PZT. The sensor/actuator is disposed on a sensor/actuator substrate. The sensor/actuator substrate is formed of a material selected for being resistive to attack by hydrofluoric acid vapor.

SUMMARY OF THE INVENTION

According to a first aspect of the invention, a system useful for dispensing medication comprises a foundation, a gripper including a first portion and a second portion spaced from the first portion, the first portion being movable toward and away from the second portion along a gripper direction, a first actuator which changes length in response to a stimulus, the first actuator partially secured to the foundation and positioned adjacent to the gripper first portion, the first actuator oriented relative to the gripper direction and positioned relative to the gripper first portion so that when the first actuator changes length in response to a stimulus the first actuator moves the gripper first portion along the gripper direction, a second actuator which changes length in response to a stimulus, the second actuator partially secured to the foundation and positioned adjacent to one of the gripper portions, the second actuator oriented relative to the gripper direction and positioned relative to said one of the gripper portions so that when the second actuator changes length in response to a stimulus the second actuator moves said one of the gripper portions along a direction different from the gripper direction.

According to a second aspect of the invention, a system useful for dispensing medication comprises a medication cartridge including a hollow barrel, and open end, and an outlet opposite the open end, a plunger slidably positioned in the barrel, a slide positioned in the barrel adjacent to the plunger and movable in the barrel along a slide direction, a first actuator which changes length in response to a stimulus, the first actuator partially secured to the slide, the first actuator oriented relative to the slide direction and so that when the first actuator changes length in response to a stimulus the first actuator moves the slide along the slide direction, and a second actuator which changes length in response to a stimulus, the second actuator partially secured to the slide, the second actuator oriented relative to the slide direction so that when the second actuator changes length in response to a stimulus the second actuator engages the barrel inside surface and holds the slide in the barrel.

According to a third aspect of the invention, a system useful for dispensing medication comprises a U-shaped flexible shaft, a solenoid movable between first and second positions, a pawl connected to the solenoid, a pinion having teeth and positioned with the pawl between the pinion teeth, a belt on the pinion, an arm attached to the belt and to the flexible shaft, wherein movement of the solenoid between the first and second positions moves the pawl, the pawl rotating the pinion, the pinion moving the belt, the belt moving the arm, the arm moving the flexible shaft.

According to a fourth aspect of the invention, a device useful for dispensing a liquid comprises a plurality of needles, the needles each including a sharpened end and being bent adjacent to the sharpened end, a base including bores in which the needles are at least partially inserted, the base including an annular space to which the bores extend, and a cap sealingly mounted to the base and forming a plenum space with the base, the plenum space including a portion of the base annular space, the cap including a fluid passageway in fluid communication with the plenum space.

It is a general object of the invention to provide a new and improved infusion pump which is adapted for use with pre-filled single dose containers and configured for use with a catheter or integrated skin interface device configured from a plurality of micro projections attached directly to the pump.

Another object of the invention is to provide a pump with an integrated skin interface device that breaches the stratum corneum with multiple hollow projections that penetrate the skin to the a depth that goes beyond the superficial vascular plexus but not as deep as the deep vascular plexus and is connected to a micro infusion device that is capable of providing a relatively constant infusion of medication or bolus injections on demand. This also provides a less painful infusion because the depth control of infusion devices of this invention do not penetrate as deep and disrupts the pain sensors in the skin. This also provides the patient a more comfortable infusion and minimizes the irritation from the infusion process Another object of the invention is the formation of the small and compact infusion or injection system that is capable of being used separately to infuse or inject medication when attached to a catheter.

Another object is to provide an infusion pump which eliminates the need for the patients to separately transfer the medications into containers used with the pump, and thereby minimize costly and difficult preparation steps.

Another object is provide an infusion pump which accurately dispenses the medication at a controlled pressure and for a controlled period of time which enables the use of a micro projection skin interface device.

Another object is to provide an infusion pump which can include a mechanical drive system that is safe, low cost, and compact in size.

Another object is to provide an infusion pump which can achieve health benefits by lowering or obviating the risk of contaminating the medication by transferring the medication from a primary container to one which is compatible with the pump and providing an alarm in the case where the solution is not completely delivered to the patient.

Another object is to provide an infusion pump that is small in size to permit discrete infusion of medication.

Another object is to provide an infusion pump which accurately dispenses medication at a controlled pressure and for a controlled period of time.

Another object is to provide an infusion pump which includes a control system with is capable of supporting both basal rate delivery and bolus delivery.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DESCRIPTION OF THE PREFERRED EMBODIMENTS

Referring to the drawing figures, like reference numerals designate identical or corresponding elements throughout the several figures.

Pumps in accordance with the present invention can be used with either a standard catheter or integrated into a delivery mechanism that has a plurality of projections for penetrating the stratum corneum.

In a first embodiment the pump is constructed with an integrated infusion device configured to breach the stratum corneum in multiple instances from a plurality of projections. These projections are configured so that they enter the subcutaneous region of the patient's skin and provides a painless means of creating a breach in the stratum corneum which is sealed against leakage by the skin surrounding each projection and provides a flow path for either a basal and bolus injection of medication.

In a second, alternate embodiment, a pump is attached to a traditional catheter that is inserted into the subcutaneous region of the patients skin and the pump is worn or attached to the patient to provide either a basal and bolus injection of medication. Alternatively, the pump is attached to a connecting tube and a drug delivery device of the invention is used to infuse the medication into the patient.

A third embodiment of the invention the pump drive system includes a solenoid that indexes the piston of the pump utilizing a rack and two pinion gears. The index distance is selected such that the index corresponds to the minimum dose per hour when distributed over a time interval which can be less than one hour. This embodiment also utilizes a U-shaped drive piston that is described in the aforementioned co-pending application Ser. No. 09/672,103.

The passage of the drug into local or systemic circulation is considered as a further or continuing result of percutaneous penetration of drug administered according to the present invention. As used herein, the term "percutaneous" means penetration through the skin to the local or systemic circulatory system by puncturing, scraping, or cutting the stratum corneum, but not puncturing, scraping, or cutting to a substantial extent, the interior layers of the skin.

A first embodiment of another aspect of the invention utilizes a skin interface device which breaches the stratum corneum with multiple lumen-containing projections and is preferably connected to a micro infusion device that is capable of providing a relatively constant infusion of medication or bolus injections on demand. Once such device is described in the aforementioned co-pending application Ser. No. 09/672,456. The skin interface device of the present invention is configured from either micro-machined components utilizing either silicon oxide, metal, or plastic substrate or small stainless steel needles arranged in an array. The needles or micro projections are preferably constructed so as to provide a slight bend or curve in the projection. When inserted into the skin the curved or bent protrusion forms a small pocket in the skin where the projection has been inserted. This pocket provides a pre-formed interstitial reservoir for the infused medication that reduces the irritation of the skin from the infusion of medication. The protrusion can either be bent at the needle tip or along the shaft of the needle or a combination of both to achieve the appropriate pocket surrounding the protrusion. Typical pockets formed in this manner range from 0.00001 to 0.001 milliliters in volume. The pockets also provide less resistance to the infused medication and therefore minimize the red marks surrounding traditional infusion catheters.

Because the projections are short and the associated fluid delivery plenum small the device eliminates the perception by the patient of pain, invasive penetration or inconvenience due to size. Additionally the device produces significantly less pain when inserted because in only enters the body between 1 and 3 millimeters from the surface of the stratum corneum. By entering the body in the abdominal area a minimum of 1 millimeters but no deeper than 3 millimeters, the projections do not cause pain due to the presence of only pressure sensing nerves in the skin in that region of the body. Additionally the depth of penetration is significant enough to insure the absorption of medication by the body is consistent with the current infusion and injection processes so that the patient and health care professionals managing the disease condition does not have to readjust the traditional therapies.

In the present invention, the combination of a micro projection system and an integrated pump or injection drug delivery device provides the patient with a discrete and convenient means of injecting or infusing medication subcutaneously into the body and solves problems associated with the current devices. By providing a close and closed communication path between the pumping mechanism, medication container and micro projection infusion device, the patient has a very small and discrete infusion or injection system capable of delivering the medication to a depth in the skin which is neither painful or presents a new infusion standard to the current infusion therapies.

The micro projections are capable of overcoming the skin's natural barrier by the formation of the tiny projections that are in communication with the fluid delivery pathways. These penetrations breach the skin's natural barriers to penetration. These include both its morphological and macromolecular organization. The small pockets created by the bend needles minimize the infusion irritation of the surrounding skin. The small size and discrete nature of the device of this invention facilitate improved treatment therapy by making it easier for the patient to administer more frequent and smaller doses of medication.

Microprojections in accordance with the present invention can be made by numerous methods. By way of example and not of limitation, the processes described in the following documents are usable to form the microprojections of the present invention.

With respect to the formation of the micro-projections, U.S. Pat. No. 5,391,250, to Cheney II et al., teaches a method of fabricating thin film electrochemical sensors for use in measuring subcutaneous or transdermal glucose. Fabrication of the sensors comprises placing a thin film base layer of insulating material onto a rigid substrate. Conductor elements for the sensors are formed on the base layer using contact mask photolithography and a thin film cover layer.

U.S. Pat. No. 5,437,999, to Diebold et al., teaches a method of fabricating thin film electrochemical devices that are suitable for biological applications using photolithography to define the electrode areas. The disclosures of each of the above patent specifications are incorporated herein by reference in their entirety specifically for the electromachining methods described in their disclosures.

An excellent reference on materials and process for fabricating electronic components is Charles A. Harper, Handbook of Materials and Processes for Electronics, 1984, Library of Congress card number 76-95803. It provides detail process information on thick film, thin film, and photo resist processes usable in the present invention.

The use of semiconductor processes for sensors is common in the literature but have not been used to form infusion cannula or skin disrupting micro penetrations. The techniques found in both U.S. Pat. Nos. 5,391,250 and 5,437,999 can be used to define infusion cannula as described in this invention or micro machined elements.

The U-shape drive piston which is described in the aforementioned co-pending application Ser. No. 09/672,103, for a mechanical injection or infusion device, can also be configured such that it can provide an automated infusion or injection by connecting the U-shaped piston to a miniature solenoid and indexing a rack and pinion drive. The compact shape of the drive mechanism found in the co-pending application Ser. No. 09/672,103 can be well-suited for delivering a pulsating or bolus medication delivery. The U-shaped piston presents a small footprint and the design of the flexible shaft can be fashioned to minimize the thickness of the resulting device.

The present invention provides numerous improvements over the existing art. The use of a small micro projections formed from curved needles and a micropump of the invention also provides a discrete means for a patient to insure that they comply with an intensive medication therapy protocol without having to be indiscreet or incur pain and discomfort.

Micro machined or micro-needles form projections which are capable of overcoming the skin's natural barrier by the formation of the tiny projections which are in communication with the fluid delivery pathways. These penetrations breach the skins natural barriers to penetration and allow for a controlled and even infusion of medication without injecting all the medication into one concentrated location. The present invention also provides an improved infusion process compared to the prior art which goes to a sufficient depth to insure that the insulin is absorbed in a controlled manner and consistent with the current subcutaneous process which the devices that only breach the stratum corneum. This gives the patient a more comfortable infusion and minimizes the irritation from the infusion process.

Turning now to the drawing figures, aspects of the present invention will now be described.

Figure 3:
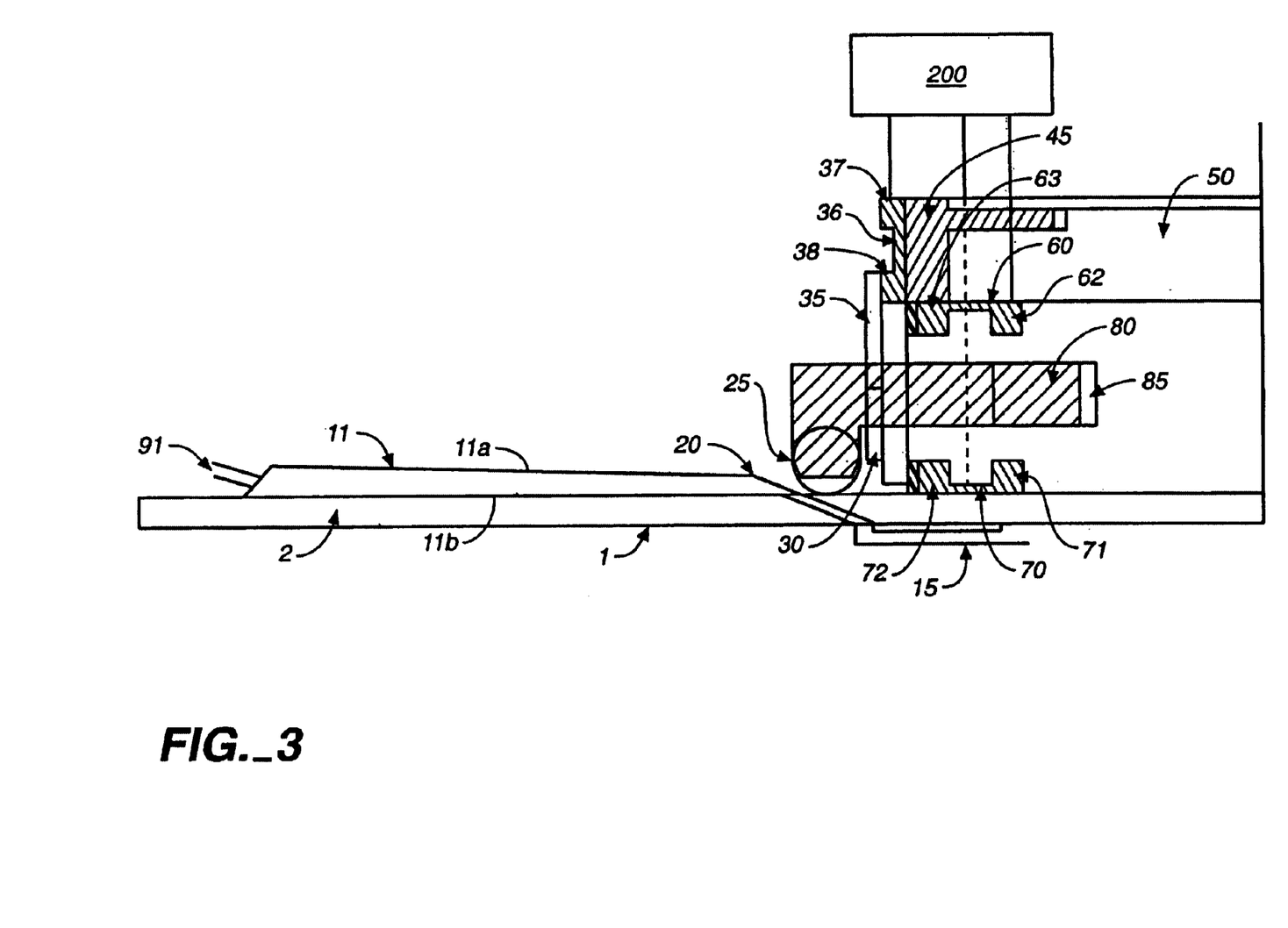
FIG. 3. illustrates an elevation view illustrating a roller version of an infusion pump in accordance with one embodiment of the invention
Figure 4:
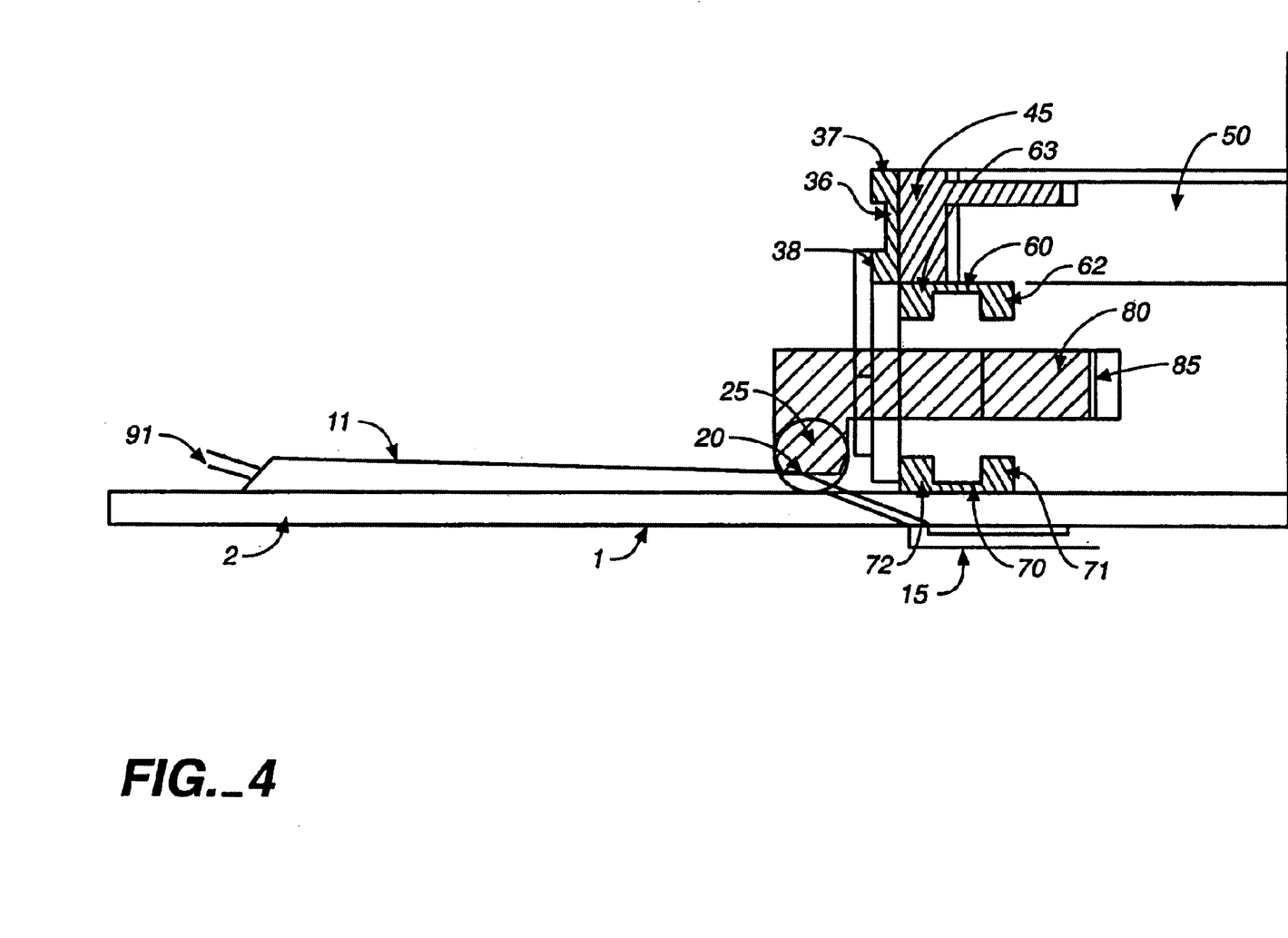
FIG. 4 illustrates an elevation view illustrating a roller version of an infusion pump in accordance with one embodiment of the invention showing the pump in FIG. 3 with the action positioned to expel fluid from the outlet.
Figure 5:
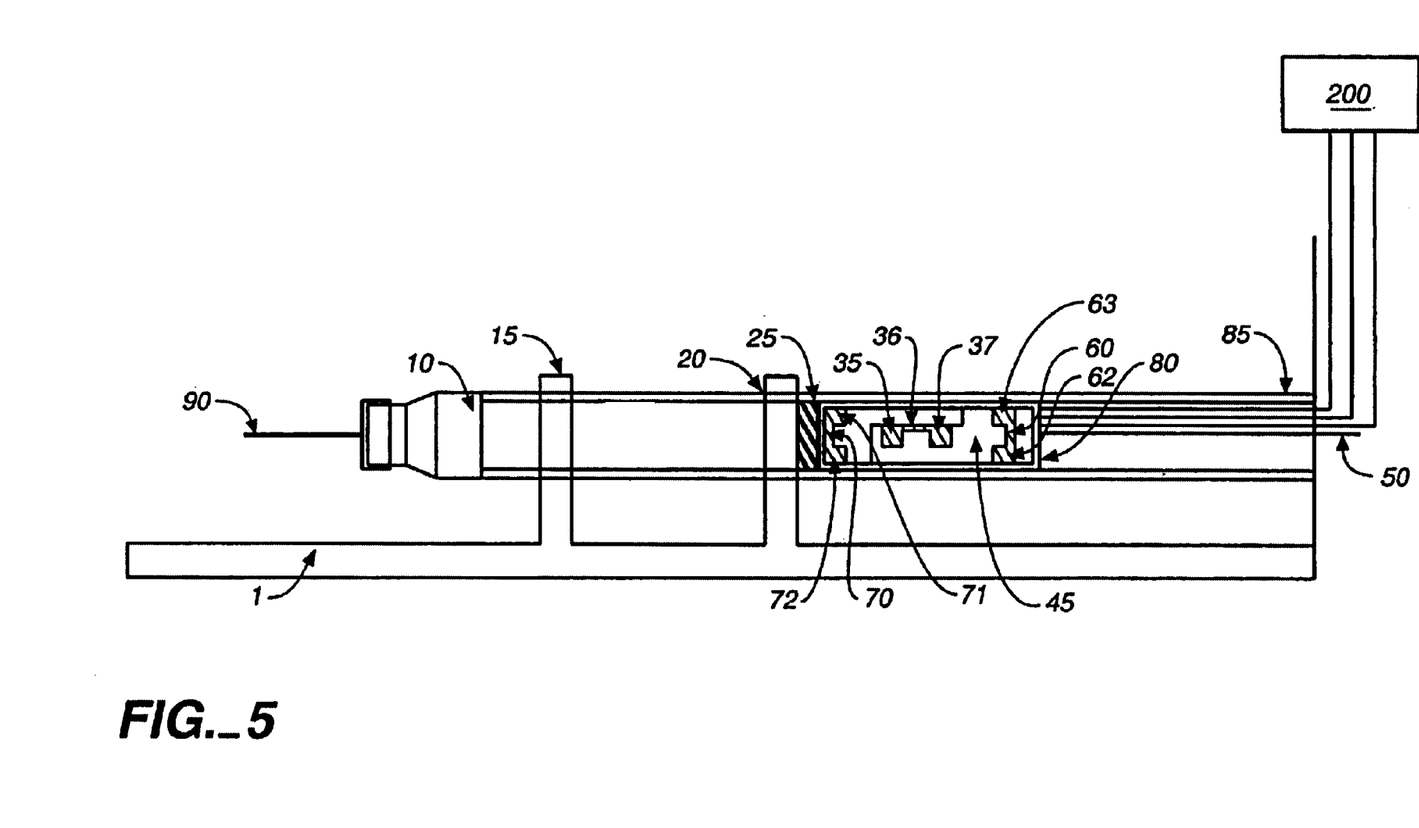
FIG. 5 illustrates an elevation view of an indexing piston version of an infusion pump in accordance with one embodiment of the invention.

In the drawings FIGS. 1–5 illustrate three exemplary embodiments of the invention. FIG. 5 illustrates an infusion pump according to a preferred embodiment of the invention.

Figure 1:
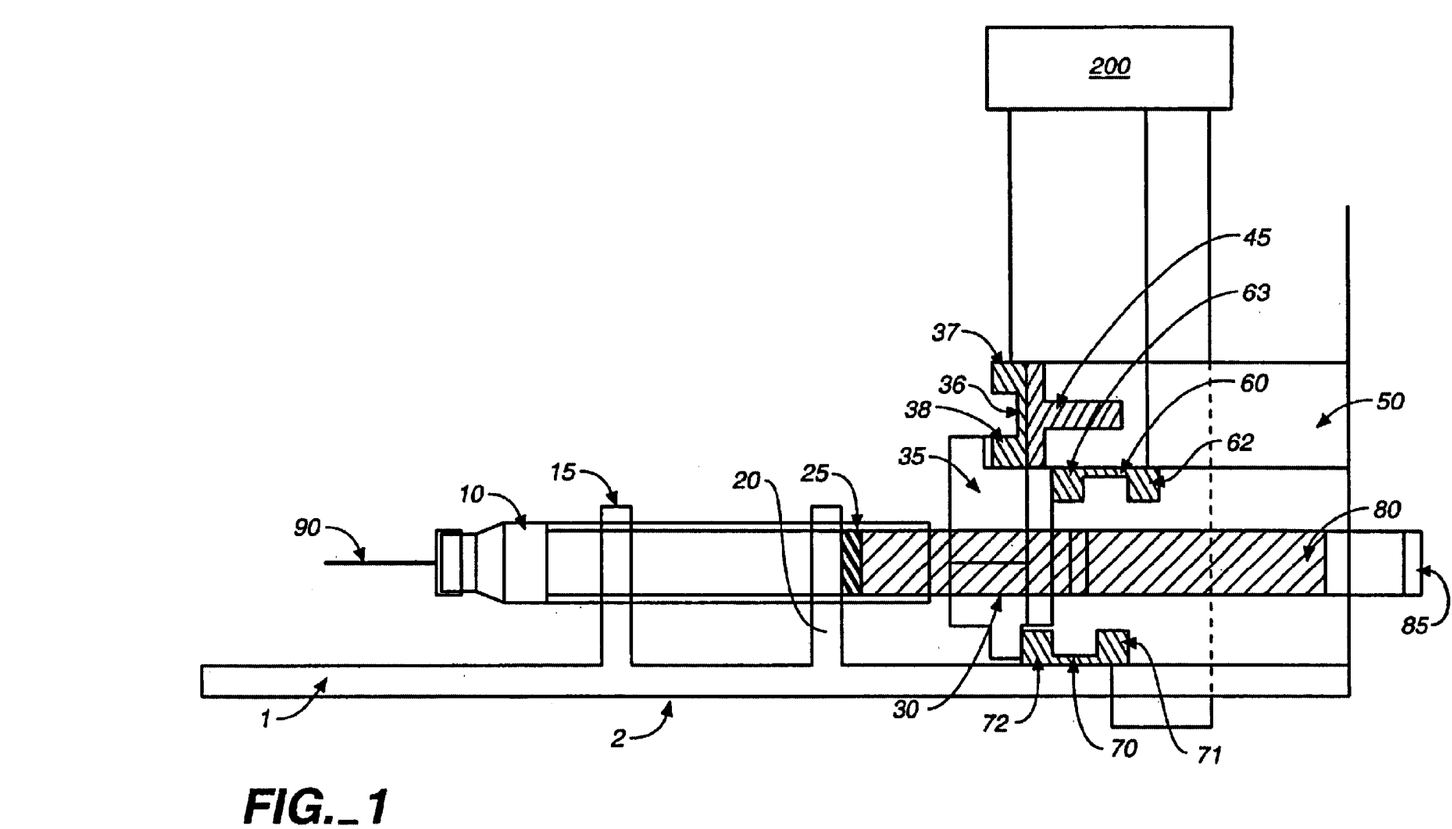
FIG. 1 illustrates a elevation view illustrating a piston version of an infusion pump in accordance with one embodiment of the invention.

FIG. 1 shows an embodiment of an infusion pump 1 which provides an infusion system which enables a patient to infuse medication with a pump 1 that uses a standard prefilled cartridge 10 and has a small profile. Infusion pump 1 includes a piston 80 guided in piston guide 85. The piston 80 is gripped by index gripper 35 and 30 that are attached to micro actuators 36, 60 and 70. The prefilled cartridge 10 is restrained in holders 15 and 20 and an outlet/needle/cannula 90 is attached to the cartridge. The prefilled cartridge 10 has a plunger 25 positioned in the barrel of the cartridge 10. Micro actuator 36 is positioned on a slide 45 that is sidably held in a foundation 50. Micro actuator 60 is positioned on foundation 50 and micro actuator 70 is position on foundation 2. Foundation 2 can also include a closeable lid so that the internal elements of the device 1 can be protected and shielded from access, while permitting access to the cartridge for replacement.

Microactuators according to some embodiments of the present invention are described in U.S. Pat. Nos. 5,644,177 and 5,914,507.

Index grippers 30, 35 can take one of numerous forms in the present invention. By way of example and not of limitation, upper gripper 35 can be in the form of a jaw of a clamp which is moved up and down relative to the piston 80. When in its lower position, gripper 35 engages the outer surface of the piston 80. Lower gripper 30 can be relatively stationary, and acts as a base against which the piston is held by the upper gripper 35. According to another embodiment, both grippers 30, 35 are formed as movable jaws of a clamp which engage substantially opposite sides of the piston 80. When both grippers 30, 35 are movable, they can be moved by separate microactuators 36 which act together and using the same control signal from controller 200. Alternatively, a single microactuator 36 can be used, and the grippers 30, 35 are joined together by structure which causes both grippers to clamp together when either one is moved. The skilled artisan is well-aware of structures useful for connecting together grippers 30, 35 in this last manner.

Figure 2:
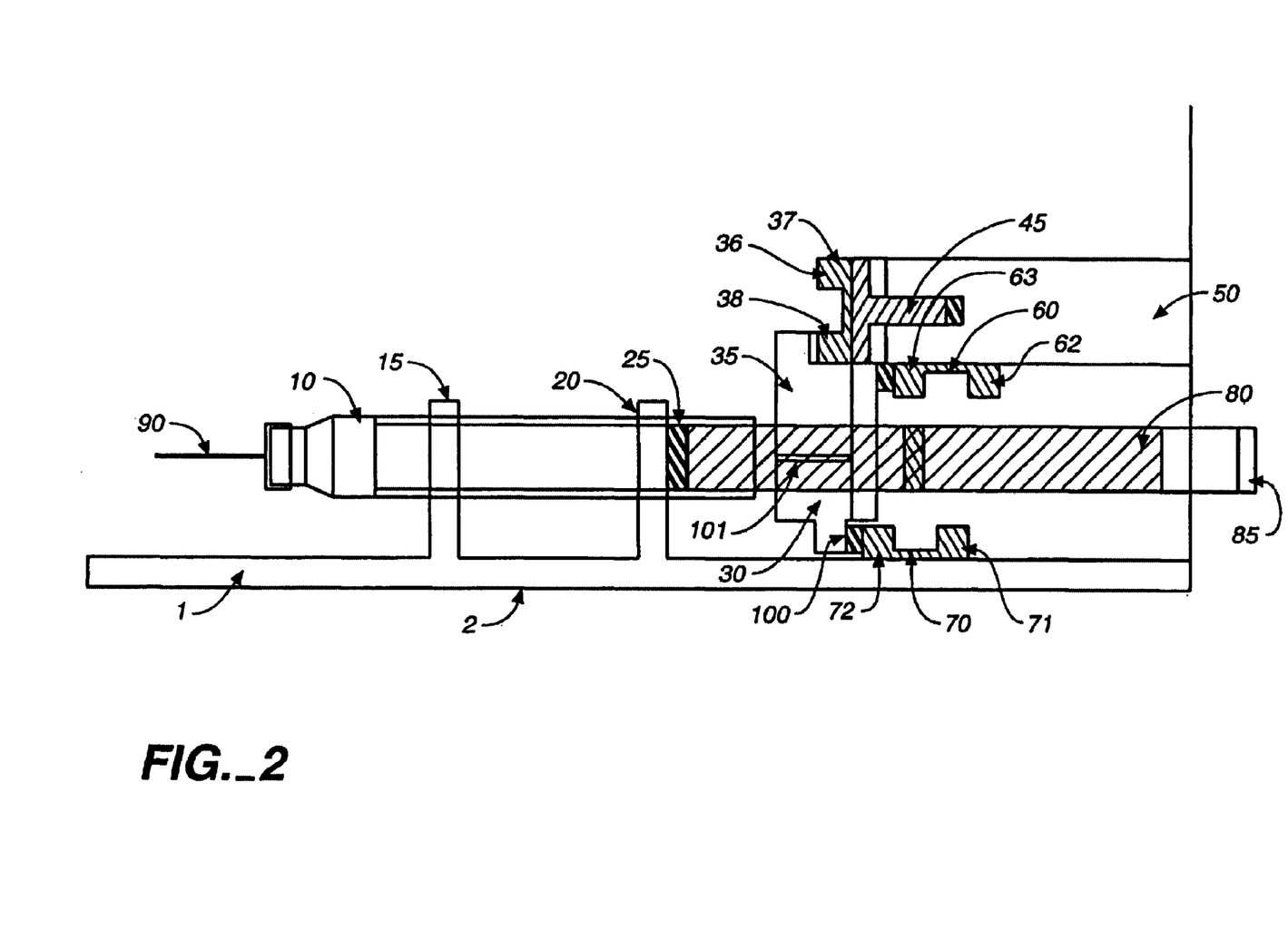
FIG. 2 illustrates an elevation view illustrating a piston version of an infusion pump in accordance with one embodiment of the invention showing the pump in FIG. 1 with the action positioned to expel fluid from the outlet.

The fluid is expelled from the prefilled cartridge 10 as show in FIG. 2. The process is a step-and-repeat process which therefore results in a pulsating infusion of medication. The pulsation can be smoothed out using various flow damping techniques if that is required for the application. The step-and-repeat process begins by the control processor 200 providing a stimulus, preferably an electrical stimulus, to microactuator 36 such that the actuator changes length, closing the index gripper including pieces 35 and 30. The stimulus can either be piezoelectric or magnetic change. The stimulus causes the index gripper to close because micro actuator 36 is fixed at end 37 and allows end 38 to move when the micro actuator is activated. This pushes and closes gripper 35 against the cartridge 10 and lower gripper 30.

The control processor 200 then provides a stimulus to micro actuators 60 and 70 such that the actuators change length, pushing the piston 80 forward. The stimulus to cause the micro actuators to expand and contract can either be piezoelectric, electric, or magnetic change. The stimulus causes the piston 80 to move forward because micro actuator 60 and 70 are fixed at ends 62 and 71 and this allows ends 63 and 72 to move when the micro actuator is activated. Ends 63 and 72 are attached to the index grippers and move the index grippers longitudinally forward and backward. Forward movement of the actuators 60, 70 pushes the piston 80 against the plunger 25 which moves a distance 100, pushing the fluid out outlet 90. The control processor then deactivates micro actuator 36 causing it to move distance 101 and return to normal length, which opens index gripper 35 and 30. The control processor then deactivates micro actuators 60 and 70 causing them to return to normal length, pulling the index grippers 35 and 30 back. The process can be repeat as often as need to index the piston forward to expel medication out of outlet 90. The Microactuators can also be configured with to include or be used as sensors to insure that adequate control of the process can be had, such as by using the sensors to feed back a control signal.

The microactuators can be manufactured from various processes, including micro element machining to form Micro Electro-Mechanical Systems (MEMs) structures that are capable of expanding and contracting when either a piezoelectric, electric, or thermal stimulus is turned on or off. In addition the invention can be configured to use of miniature electromechanical solenoids that are actuated by applying the appropriate electrical, magnetic or piezoelectric stimulus. Any of these will result in a safe operating device due to the need to complete one full cycle to achieve an index.

The problems associated with medication delivery applications focus on the problem of not controlling the infusion/injection process. By requiring an On then Off discrete signal to achieve one cycle, as in embodiments of the present invention, the issue is resolved. If the processor or mechanical device controlling the device becomes locked in one signal mode the result can, in the worst case, only cause one infusion cycle corresponding to one index amount.

FIGS. 3 and 4 show an alternate embodiment of Infusion pump 1 provides an infusion system which enables a patient to infuse medication with a pump 1 that uses a standard prefilled bag 11 having sidewalls 11a, 11b, and has a small profile. Infusion pump 1 includes a piston 80 guided in piston guide 85 which is attached to roller 25. The piston 80 is gripped by index gripper 35 and 30 that are attached to micro actuators 36, 60 and 70. The prefilled bag 11 is restrained in holders 15 and 20 and an outlet 91 is attached to the bag. Micro actuator 36 is position on slide 45 that is held in foundation 50. Micro actuator 60 is positioned on platen or foundation 50 and micro actuator 70 is position on platen or foundation 2.

The fluid is expelled from the prefilled bag 11 as show in FIG. 4. The process is a step and repeat process and therefor results in a pulsating infusion of medication. The pulsation can be smoothed out using various flow damping techniques if that is required for the application. The step and repeat process begins by the control processor 200 provides a stimulus to micro actuator 36 such that the actuator changes length closing the index gripper comprised of piece 35 and 30. The stimulus can either be piezoelectric, electric or magnetic change. The control process is similar to that used by embodiment shown in FIG. 1. The roller is pushed along the length of the bag 11 along one of the sidewalls, pressing the contents of the bag out of the outlet 90.

FIG. 5 shows that a preferred embodiment of Infusion pump 1 provides an infusion system which enables a patient to infuse medication with a pump 1 that uses a standard prefilled cartridge 10 and has a small profile. Infusion pump 1 includes a piston 80 guided in piston guide 85. The piston 80 is indexed by an index gripper formed by micro actuators 60 and 70 and indexing actuator 36 which are positioned inside piston 80. The micro actuators 36, 60 and 70 are electrically connected to control processor 200. The prefilled cartridge 10 is restrained in holders 15 and 20 and an outlet 90 is attached to the cartridge. The prefilled cartridge 10 has a plunger 25 position in the cartridge 10. Micro actuator 36 is positioned on slide 45 that is held inside of piston 80. Micro actuator 60 and micro actuator 70 are positioned such that their free ends can engage and grip the inner dimensions of the inner surface of the barrel of the prefilled cartridge 10.

The fluid is expelled from the prefilled cartridge 10 by alternately activating the micro actuators 70, 60 and 36. The process is a step-and-repeat process and therefor results in a pulsating infusion of medication. The pulsation can be smoothed out using various flow damping techniques if that is required for the application. The step-and-repeat process begins by the control processor 200 providing a stimulus to micro actuator 60 such that the actuator changes length causing the end of piston 80 with micro actuator 60 to expand and grip the inner dimension of cartridge 10. The stimulus can either be piezoelectric or magnetic change. The stimulus causes the index gripper to open because micro actuator 60 is fixed at the center of the actuator which allows ends 63 and 62 to move when the micro actuator is activated. This allows the actuator to grip against the cartridge 10. The control processor 200 then provides a stimulus to micro actuators 36 such that the actuator change length pushing the internal slide 45 in piston 80 forward. The stimulus can either be piezoelectric, electric or magnetic change. The stimulus causes the piston 80 to move forward because micro actuator 36 is fixed its center, which allows ends 35 and 37 to move when the micro actuator is activated. This pushes the piston 80 against the plunger 25 that pushes the fluid out outlet 90.

The control processor 200 then provides a stimulus to micro actuator 70 such that the actuator changes length, causing the end of piston 80 with micro actuator 70 to expand and grip the inner dimension of cartridge 10. The stimulus can either be piezoelectric or magnetic change. The stimulus causes the index gripper to open because micro actuator 70 is fixed at the center of the actuator which allows ends 71 and 72 to move when the micro actuator is activated. This allows the actuator to grip against the inner surface of the barrel of cartridge 10. The control processor 200 then deactivates micro actuator 60 causing it to return to normal length which disengages the gripper from the cartridge 10. The control processor then deactivates micro actuators 36 causing it to return to normal length pulling the rear end of the piston 80 forward. The process can be repeated as often as need to index the piston forward to expel medication out of outlet 90. The microactuators can also be configured with sensors (not illustrated) to insure adequate control of the process. Further optionally, the feedback voltage, current, or the like from the actuator can be used as an indication of the state of the actuator for control of the actuators. The piston is retracted when the medication has been emptied from cartridge 10 by the patient pulling on cable 50.

The pump in all embodiments dispenses solution under pressure at a relatively constant flow rate for designated periods of time, and provides a more sterile environment then existing pumps. Visual indicators and audible alarms can further optionally be provided so that the process can be monitored. The infusion pump is also relatively compact and lightweight so that it can be used by any patient.

Figure 6:
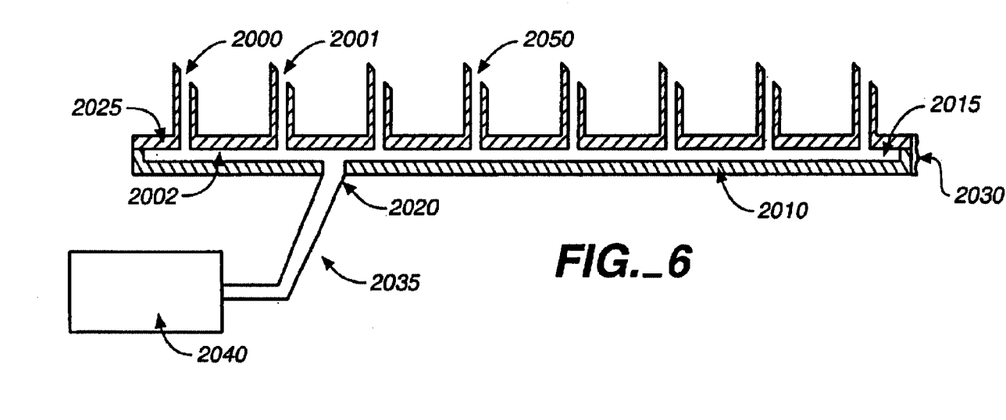
FIG. 6 illustrates an elevation view of the micromachined projections of the skin interface device.
Figure 11:
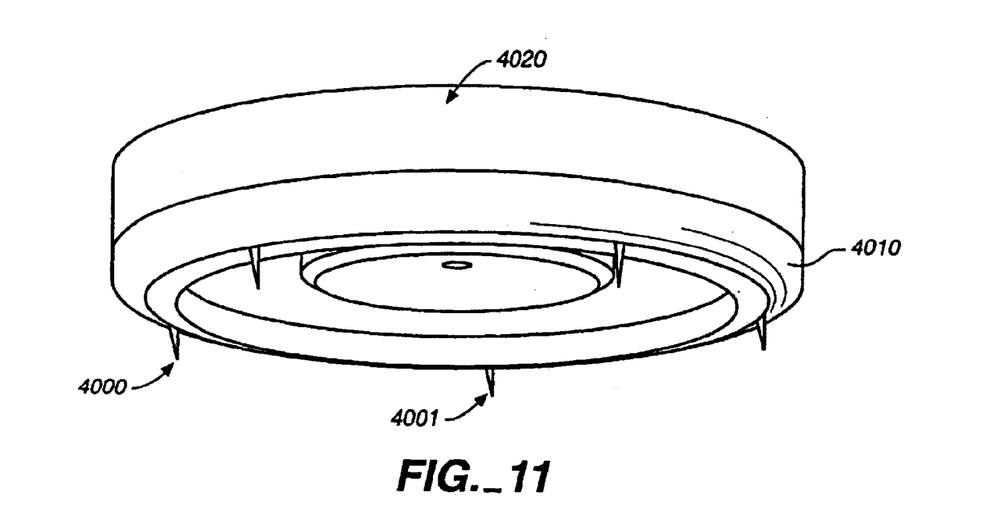
FIG. 11 illustrates a perspective view of an array of small stainless steel needles configured in a microprotrusion device.

FIG. 6 is an elevation view of the micro-machined projections of a skin interface device. The projections are formed from either semiconductor materials or micro stainless steel needles. When manufacturing the needles from semiconductor materials, one fabricates them by applying photo resist and etching the configurations into the wafer or by using an array of small stainless steel needle as shown in FIG. 11. The micro-machined projections can be made any length by adding material to the projections by plating gas discharge or sputtering operations and reapplying a photo resist to etch the geometries into the layers.

The micro machine projections 2000 are built up from a series of etching and deposition steps that form the cannula shape micro projection 2000 with the fluid delivery hole 2001. The plenum 2002 is formed by attaching an etched part 2010 that is has the plenum 2015 and the feed port 2020 and attaching it to the cannula holder 2025, such as with adhesive 2030. The feed port is then attached to a catheter connecting tube 2035 or directly to the pump 2040. The materials which can be used to fabricate the skin interface device 2050 include, but are not limited to, silicon oxide, gold, silver, carbon, or any other material which is capable to be deposited or machined with semiconductor or chemical methods.

Figure 7:
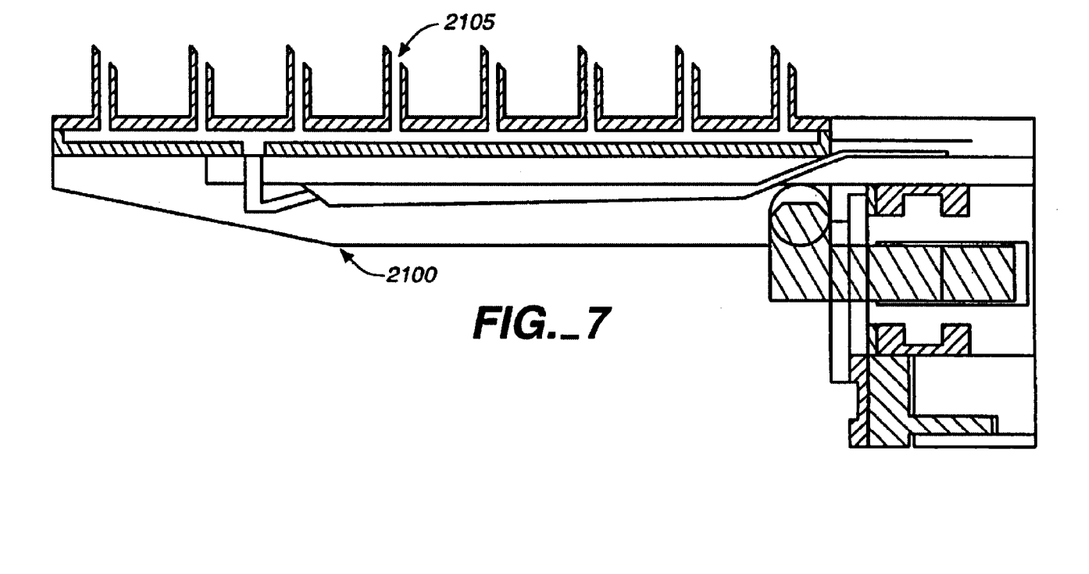
FIG. 7 illustrates a drawing on a pump of the present invention which has a skin interface device mounted in direct communication
Figure 8:
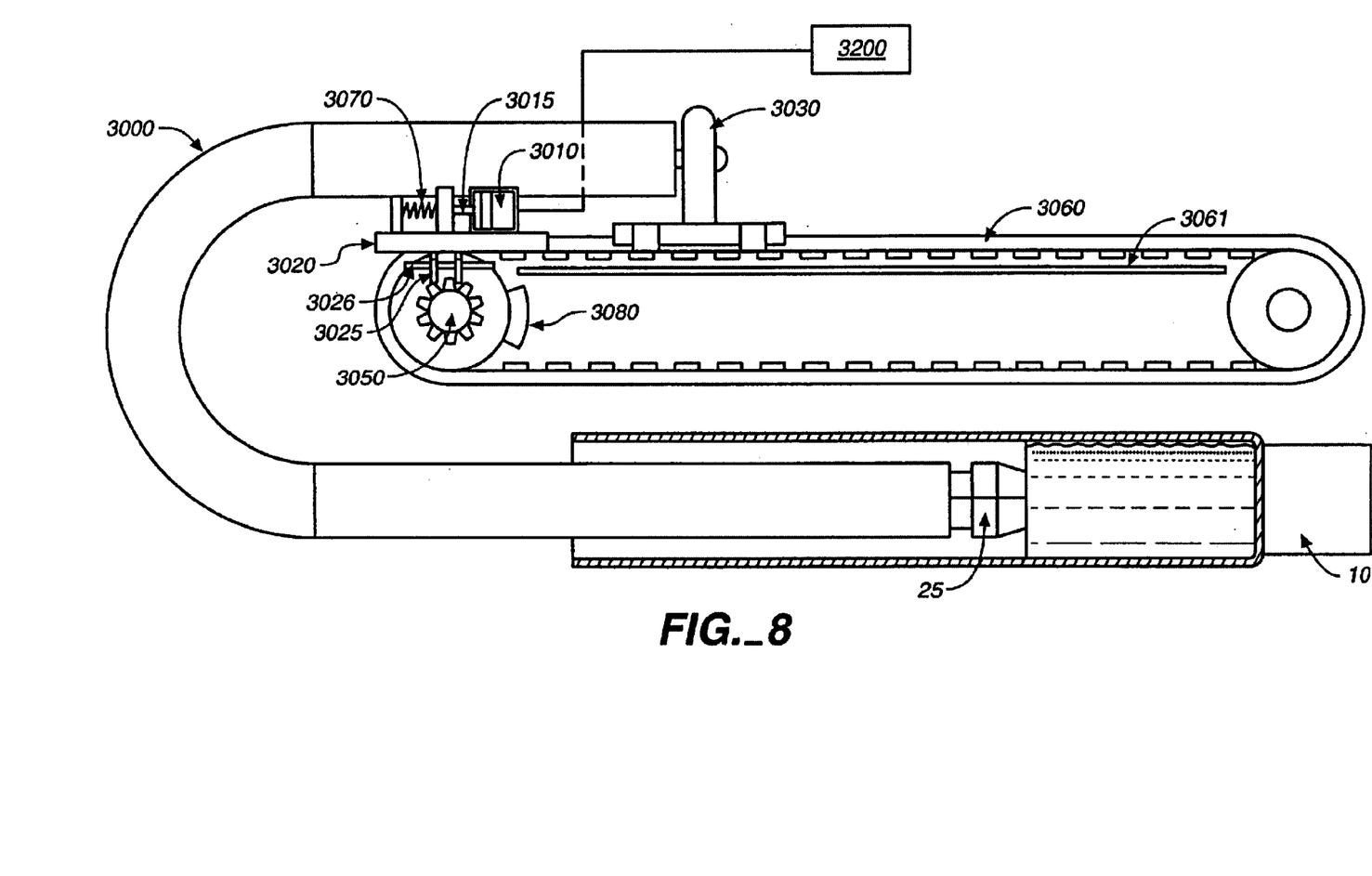
FIG. 8 illustrates a miniature solenoid drive mechanism for an infusion device of the present invention.

FIG. 7 is a drawing on a pump 2100 of the present invention which has a skin interface device 2105 mounted in direct communication FIG. 8 illustrates a pump of the present invention that utilizes a flexible shaft 3000 and miniature solenoid 3010 to drive the plunger 25 positioned in the medication cartridge 10. The flexible shaft 3000 can be a flexible shaft such as that described in the aforementioned '103 application. The miniature solenoid 3010 includes a solenoid push rod 3015 that pushes on a rack 3020 which indexes arm 3030. The pawls 3025 attached to the bottom of the rack 3020 are locked due to the overturning moment created by the force on the pawls 3025 attached to rack 3020. This indexes pinion gear 3050 (counterclockwise in the illustration of FIG. 8) which drives the indexing belt 3060 riding on support 3061 and pushes on the flexible shaft 3000 which pushes on the plunger 25.

When the solenoid 3010 is energized it extends push rod 3015 which drives the indexing belt 3060. Pawls 3025 are flexible or are hinged to the rack 3020. When the pawls are pulled back by the deactivation of the solenoid 3010, the pawls retract and bend, flex, or hinge over cams 3026, which are part of pinion 3050. According to an exemplary embodiment of the present invention, cams 3026 can be formed by a slotted plate through which the pawls 3025 extend, the rack 3020 moving with the plate. With the slots extending in the direction of motion of the rack, and the pawls extending through the slots at one end of the slots, the pawls are prevented from flexing in one direction, and being free to flex and move in the other (longitudinal) direction. Thus, when the solenoid 3010 is de-energized the push rod 3015 is driven in reverse by spring 3070 and the pawls 3025, attached to rack 3020, are flexed and displaced to ride over the teeth of the pinion 3050, and therefore pinion gear 3050 is not rotated upon reverse movement of the rack 3020. The pawls' retraction force is counteracted by a friction brake 3080. Each index of solenoid 3010 equates to expressing the minimum volume of medication per time period desired. The pump's solenoid 3010 is activated by the microprocessor 3200 base on a timer set to deliver the selected dosage rate divided by the dose delivered per solenoid stroke. By way of example and not of limitation, if the pump was designed to deliver a minimum of 0.5 units of insulin per hour and a maximum of 30 units per hour the stroke of solenoid 3010 would result in a 0.5 units being expelled from cartridge 10 for every stroke. The solenoid would activate once per hour for a infusion rate of 0.5 units per hour and 60 times an hour for an infusion rate of 30 units per hour.

Many patients find that the infusion site forms small red marks that are the result of irritation from the infusion at a single point. Infusing the medication either by bolus injection or reducing the amount of medication infused at any one specific site relieves this irritation. The present invention also provides an injection device that is formed from numerous micro projections that can result in three significant improvements over the prior art. The first is the reduction and elimination in certain patients of irritation marks from the infusion of medication to one site. The second is the reduction in the bulk of the infusion hub at the patient's skin. This results in a more convenient and discrete package for the patient. The third benefit is the reduction in pain felt by the patient when inserting the infusion device.

Figure 9:
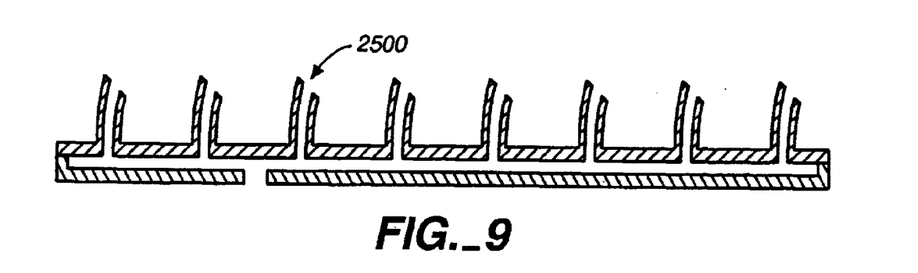
FIG. 9 illustrates the cannula including the bend in the shaft.
Figure 10:
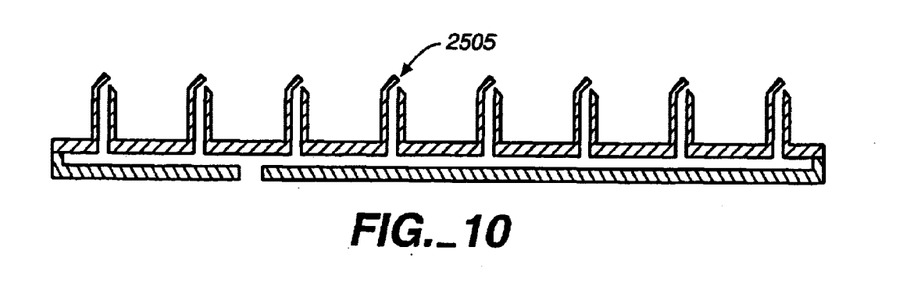
FIG. 10 illustrates the bend in the needle point to form an infusion pocket.

The small micro projections 2500 can be formed such that they have a slight curve in the direction of penetration (see FIG. 9). This has added benefit by reducing the amount of irritation from the infusion because a small pocket in the skin is formed by the curve in the cannula as shown in FIG. 9 and FIG. 10. The same beneficial affect can be achieved when using traditional needles and forming either a curve in them or adjusting the point 2505 so it forms an angle with the shaft between 1 and 25 degrees, preferably 10 degrees.

Figure 12:
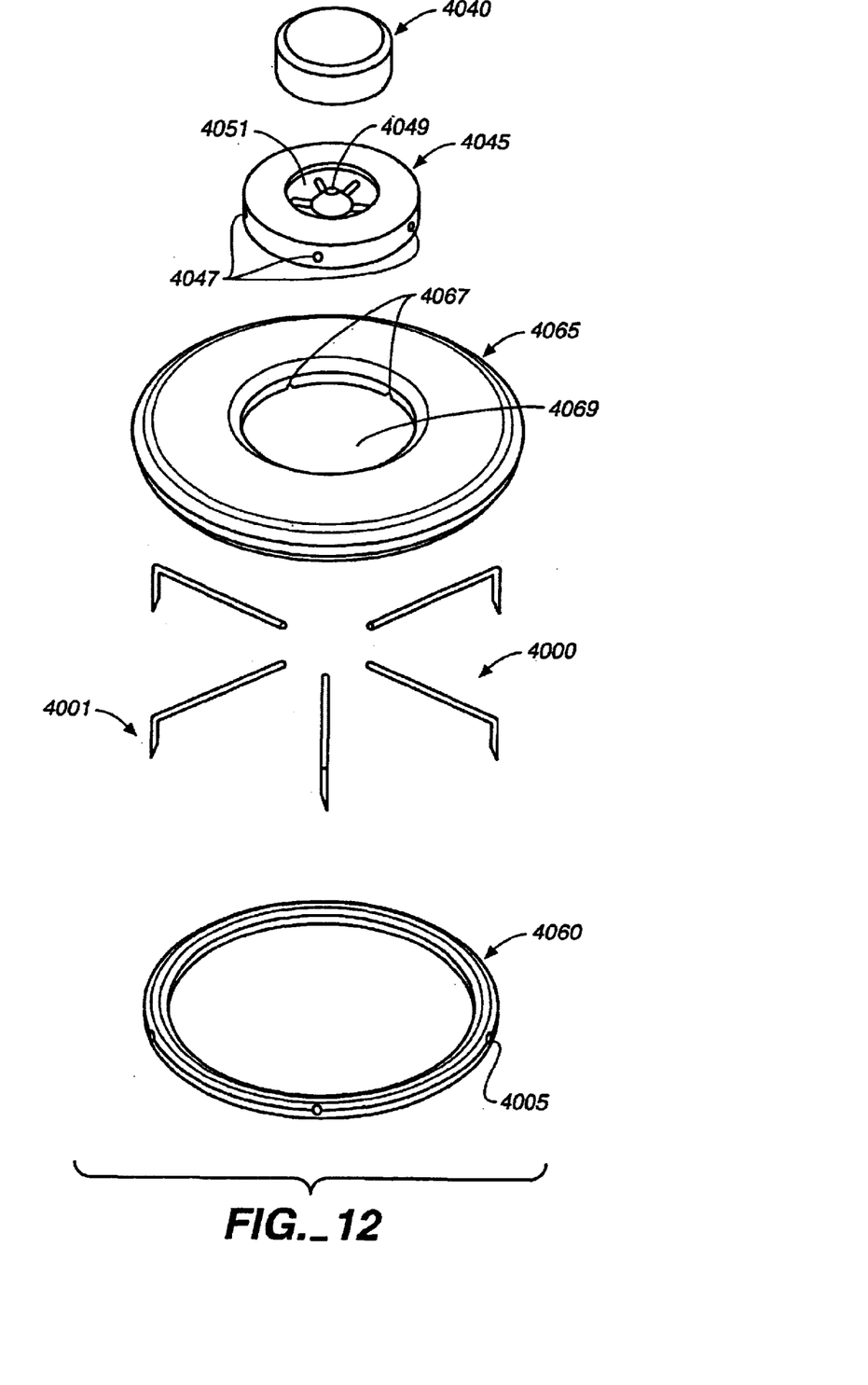
FIG. 12 illustrates a exploded view of an array of small stainless steel needles configured as a microprotrusion device.
Figure 13:
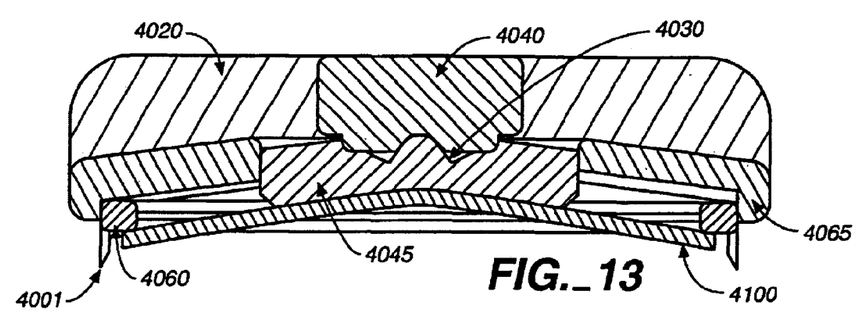
FIG. 13 illustrates a cross-sectional view of an array of small stainless steel needles configured as a micro protrusion device.
Figure 14:
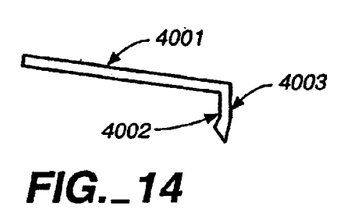
FIG. 14 illustrates a cannula showing the bend in the shaft.
Figure 15:
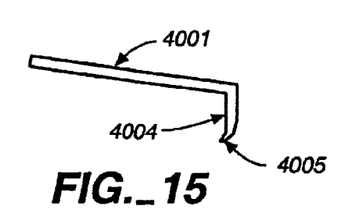
FIG. 15 illustrates shows the bend in the needle point designed to form an infusion pocket.
Figure 16:
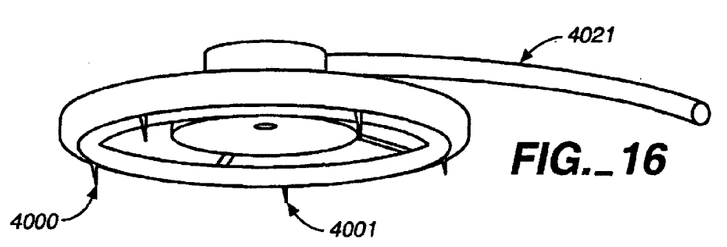
FIG. 16. illustrates a perspective view of an array of small stainless steel needles configured as a micro protrusion device.
Figure 17:
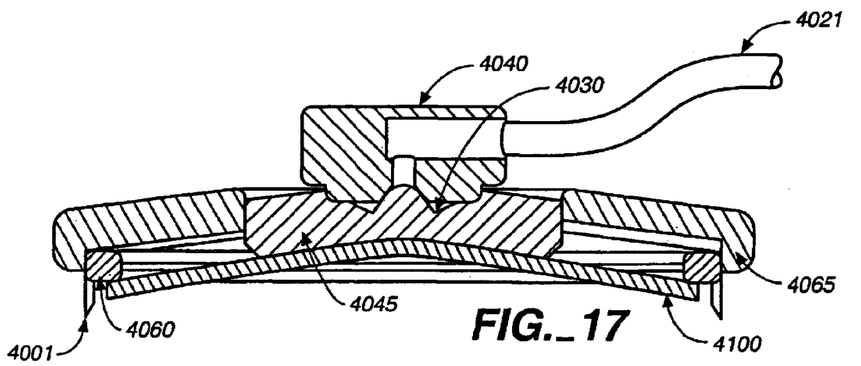
FIG. 17 illustrates a cross-sectional view of an array of small stainless steel needles configured in a microprotrusion device.

FIGS. 11–17 illustrate a device of this invention that uses an array 4000 of micro (e.g., stainless steel) needles 4001 that are fixtured in a hub 4010 which is connected to a pump/infusion device 4020, either directly as illustrated in FIG. 11 or, as illustrated in FIGS. 16 and 17, through a connecting tube 4021. The needles 4001 have an insertion length which is from 0.5 to 3 mm, depending on the insertion location which the device is designed to be used on. The bending of the needles, if provided, is similar in design to those fabricated with electro machining techniques having either a bent shaft or bent tip to form an interstitial pocket in the skin, as shown in FIGS. 14 and 15. The needles 4001 are positioned in an array so as to minimize the overall footprint but also minimize the size. The number of needles 4001 used in the array is dependent on the amount of material to be infused and the size of the interstitial pocket formed by the bent needles 4001 in the skin.

A plenum 4030 is designed to provide uniform flow to the outflow needles 4001 by being formed in a conical pattern with a conical cap 4040 and disk-shaped base 4045. The thin cross section of plenum 4030 and conical shape balance the flow so that each needle 4001 in communication with the plenum 4030 flow is essentially uniform. The base 4045 includes a number of radially extending bores 4047 into which the blunt ends of the needles 4001 are at least partially inserted. The bores 4047 open at their radially inner ends to an annular space 4051 in the center of which is positioned an upstanding cone or frustocone 4049. Cone 4049, when the base 4045 is assembled with the cap 4040, engages with projections on the bottom of the cap to form a sealed plenum as described above.

The needles 4001 extend from the bottom side of an annular member 4065 from 0.5 to 3 mm. According to one embodiment of the present invention, each needle 4001 is between 0.005 to 0.030 inches in diameter and designed to be compatible with the fluid being dispensed. The needles 4001 can be bent by placing a ring 4060 over the annular member 4065 with the base 4045 in the hole 4069 in the annular member 4065. The ring 4060 displaces or bends the ends of the needles 4001 around curved channels 4005 formed in the outer surface of the ring 4060, which channels then hold the needles 4001. The pump 4020 is therefore in direct communication with the array 4000 through a fluid passage through cap 4040 such that the medication flows from the outlet of the pump 4020 directly into the flow plenum 4030 through a connecting tube (not illustrated). Adhesive tape 4100 may be provided to insure that the pump 4500 and needle array 4000 stay attached to the patient.

FIG. 14 illustrates a stainless steel needle 4001 that is formed with a bend 4002 in the shaft 4003 and is further formed to be incorporated in an array 4000 to form and infusion device. FIG. 15 illustrates the bend 4004 in the needle 4001 point 4005 designed to form an infusion pocket in the skin of a patient.

While the invention has been described in detail with reference to preferred embodiments thereof, it will be apparent to one skilled in the art that various changes can be made, and equivalents employed, without departing from the scope of the invention. The disclosures of each of the aforementioned published documents are incorporated herein by reference in their entirety.

What is claimed is:

1. A device useful for dispensing a liquid comprising:
    a plurality of needles, the needles each including a sharpened end and being bent adjacent to the sharpened end;
    a base including bores in which the needles are at least partially inserted, the base including an annular space to which the bores extend;
    a cap sealingly mounted to the base and forming a plenum space with the base, the plenum space including a portion of the base annular space, the cap including a fluid passageway in fluid communication with the plenum space.

2. A device in accordance with claim 1, further comprising:
    an annular member having a center hole, the base positioned in the center hole.

3. A device in accordance with claim 2, further comprising:
    a ring positioned against the needle bends, the needles positioned between the ring and the annular member, the needle sharpened ends extending past the ring.

4. A device in accordance with claim 3, wherein the needle sharpened ends extend past the ring a distance between about 0.5 mm and about 3.0 mm.

5. A device in accordance with claim 11, wherein the needle sharpened ends are bent between at and angle between about 1 degree and about 25 degrees.

* * * * *